US00PP29251P2

(12) United States Plant Patent
Braeunig

(10) Patent No.: US PP29,251 P2
(45) Date of Patent: Apr. 17, 2018

(54) ***PENSTEMON* PLANT NAMED 'FLORPENMAG'**

(50) Latin Name: *Penstemon hartwegii*
Varietal Denomination: Florpenmag

(71) Applicant: Florensis B.V., Hendrik-Ido-Ambacht (NL)

(72) Inventor: Tobias M. Braeunig, Quedlinburg (DE)

(73) Assignee: Florensis B.V., Hendrick-Ido-Ambacht (NL)

( * ) Notice: Subject to any disclaimer, the term of this patent is extended or adjusted under 35 U.S.C. 154(b) by 0 days.

(21) Appl. No.: 15/530,251

(22) Filed: Dec. 15, 2016

(51) Int. Cl.
*A01H 5/02* (2006.01)

(52) U.S. Cl.
USPC ..... Plt./465

(58) Field of Classification Search
USPC ..... Plt./263.1, 465
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Penstemon* plant named 'Florpenmag', characterized by its deep purplish-red and white colored flowers, medium green-colored foliage, and vigorous, upright growth habit, is disclosed.

1 Drawing Sheet

Latin name of genus and species of plant claimed: *Penstemon hartwegii.*

Variety denomination: 'Florpenmag'.

BACKGROUND OF THE INVENTION

The present invention relates to a new and distinct cultivar of *Penstemon* plant botanically known as *Penstemon hartwegii* and hereinafter referred to by the cultivar name 'Florpenmag'.

The new cultivar originated in a controlled breeding program in Quedlinburg, Germany during July 2011. The objective of the breeding program was the development of a *Penstemon* cultivar having large flowers and a long flowering season.

The new *Penstemon* cultivar is the result of open-pollination. The female (seed) parent of the new cultivar is the proprietary *Penstemon hartwegii* breeding selection coded 2525-1, not patented, characterized by its medium burgundy-colored flowers, medium green-colored foliage, low growth vigor and upright growth habit. The male (pollen) parent of the new cultivar is unknown. The new cultivar was discovered and selected as a single flowering plant within the progeny of the above stated open-pollination during September 2012 in a controlled environment in Quedlinburg, Germany.

Asexual reproduction of the new cultivar by terminal stem cuttings since September 2012 in Quedlinburg, Germany and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Florpenmag' as a new and distinct cultivar of *Penstemon* plant:

1. Deep purplish-red and white colored flowers;
2. Medium green-colored foliage; and
3. Vigorous, upright growth habit.

Plants of the new cultivar differ from plants of the female parent primarily in flower color and growth vigor.

Of the many commercially available *Penstemon* cultivars, the most similar in comparison to the new cultivar is Polaris Purple 'Florpenpur', not patented. However, in side by side comparisons, plants of the new cultivar differ from plants of 'Florpenpur' in at least the following characteristics:

1. Plants of the new cultivar have more red in the flower color than plants of 'Florpenpur'; and
2. Plants of the new cultivar are more vigorous than plants of 'Florpenpur'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Florpenmag' The plants were approximately 20 weeks old and grown in 1.7 gallon containers. Plants were finished outdoors for 10 weeks in West Chicago, Ills. Plants were given two pinches prior to transplant.

DETAILED BOTANICAL DESCRIPTION

Figure 1:
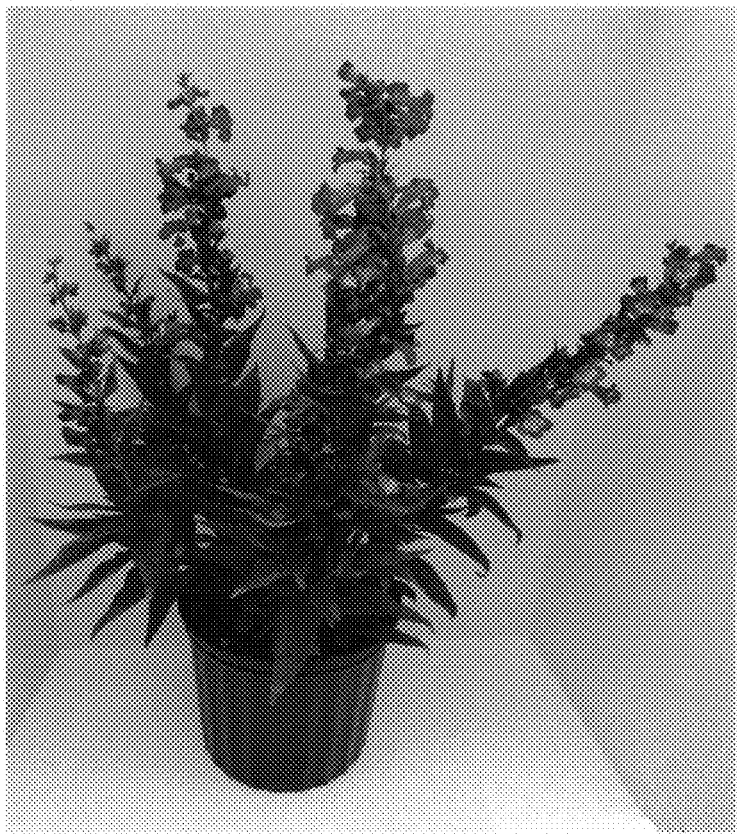
FIG. 1 illustrates a side view of the overall growth and flowering habit of 'Florpenmag'.
Figure 2:
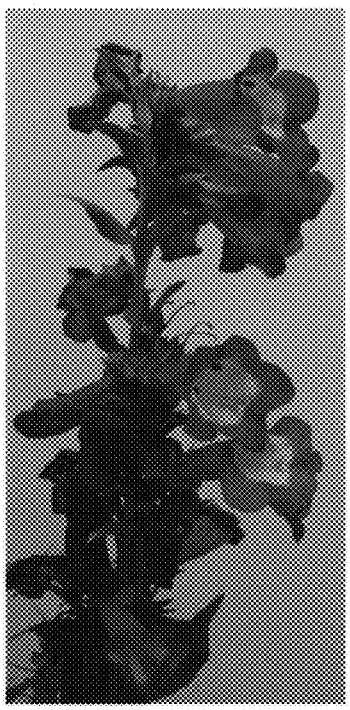
FIG. 2 illustrates a close-up view of an inflorescence of 'Florpenmag'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2016 under natural light conditions in West Chicago, Ill.

The following descriptions and measurements describe plants produced from cuttings from stock plants and grown under conditions comparable to those used in commercial practice. The plants were grown utilizing a soilless growth medium in 1.7 gallon containers for approximately 20 weeks. Plants were given two pinches prior to transplant. For approximately 8 weeks after transplant, greenhouse temperatures were maintained at approximately 60° F. (15.6° C.) during the day and approximately 55° F. (12.8° C.) during the night. For the final 10 weeks, plants were grown outside in West Chicago, Ill. No supplemental lighting was provided. Measurements and numerical values represent averages of typical plants.

Botanical classification: *Penstemon hartwegii* cultivar Florpenmag.

Parentage:

*Female parent*.—Proprietary *Penstemon hartwegii* breeding selection coded 2525-1, not patented.

*Male parent*.—Unknown.

Propagation:

*Type cutting*.—Terminal stem.

*Time to initiate roots*.—Approximately 10 to 12 days.

*Time to produce a rooted cutting*.—Approximately 5 to 6 weeks.

*Root description*.—Fine to medium, fibrous white to light brown in color.

*Rooting habit*.—Freely branching.

Plant description:

*Commercial crop time*.—Approximately 10 to 12 weeks from a rooted cutting to finish in a 15 cm pot.

*Growth habit and general appearance*.—Perennial; Vigorous, upright growth habit.

*Hardiness*.—USDA Zones 5 to 9.

*Size*.—Height from soil level to top of plant plane: Approximately 62.0 cm. Width: Approximately 60.0 cm.

*Branching habit*.—Freely branching. Pinching enhances lateral branching. Quantity of branches per plant: Approximately 6.

*Branch*.—Shape: Round. Strength: Strong. Length to base of peduncle: Approximately 29.0 cm. Diameter: Approximately 5.0 mm. Length of central internode: Approximately 3.0 cm. Texture: Densely pubescent with very short hairs. Color of young stem: 145B. Color of mature stem: 145A.

Foliage description:

*General description*.—Quantity of leaves per branch: Approximately 24. Fragrance: None detected. Form: Simple. Arrangement: Opposite and decussate.

*Leaves*.—Aspect: Acute angle to stem occasionally tips downward turning. Shape: Narrowly ovate. Margin: Shallowly serrate. Apex: Acute. Base: Sessile. Venation pattern: Pinnate. Length of mature leaf: Approximately 13.0 cm. Width of mature leaf: Approximately 4.0 cm. Texture of upper and lower surfaces: Glabrous. Color of upper surface of young and mature foliage: 137A with venation of 146D. Color of lower surface of young and mature foliage: Closest to 138A with venation of 146D.

Flowering description:

*Flowering habit*.—'Florpenmag' is freely flowering under outdoor growing conditions blooming from late spring through late summer.

*Lastingness of individual floret*.—Approximately 6 to 7 days.

Inflorescence description:

*General description*.—Type: Terminal raceme, not persistent. Quantity of open inflorescences per plant: Approximately 6. Fragrance: None detected. Length or height of inflorescence: Approximately 30.0 cm. Width of inflorescence: Approximately 10.0 cm. Quantity of fully-open flowers per inflorescence: Approximately 14.

*Peduncle*.—Strength: Strong. Aspect: Erect. Length: Approximately 3.5 cm. Diameter: Approximately 4.0 mm. Texture: Densely glandular pubescent. Gland color: Colorless, transparent, hairs 71A. Color: 145A, appears to have a reddish overlay due to pubescence color.

Flower description:

*Type*.—Single, zygomorphic.

*Bud*.—Rate of opening: Generally takes 3 to 4 days for bud to progress from first color to fully open flower.

*Bud just before opening*.—Shape: Obovoid. Length: Approximately 1.5 cm. Diameter: Approximately 9.0 mm. Texture: Densely glandular pubescent. Gland color: Colorless, transparent. Color: Calyx of 138A; petals of 71A.

*Corolla*.—Shape: Bilabiate, upper lip of two lobes and lower lip having three lobes. Width: Approximately 3.6 cm. Length: Approximately 3.4 cm. Depth: Approximately 3.5 cm.

*Upper lip lobes*.—Shape: Ovate. Margin: Entire. Apex: Broadly acute. Length from throat: Approximately 1.0 cm. Width: Approximately 1.2 cm. Texture of upper surface: Glabrous. Texture of lower surface: Sparsely glandular pubescent. Gland color: Colorless, transparent. Color of upper surface when first and fully open: 71A to 71B with a band of 72B where color transitions at throat. Color of lower surface when first and fully open: 71A.

*Lower lip lobes*.—Shape: Ovate. Margin: Entire. Apex: Broadly acute to rounded. Length from throat of central lobe: Approximately 1.0 cm. Width of central lobe: Approximately 1.5 cm. Length from throat of lateral lobes: Approximately 1.1 cm. Width of lateral lobes: Approximately 1.6 cm. Texture of upper surface: Glabrous. Texture of lower surface: Moderately glandular pubescent. Gland color: Colorless, transparent. Color of upper surface when first and fully open: 71A to 71B with a narrow band of 72B where color transitions at throat. Color of lower surface when first and fully open: 71A.

*Corolla tube*.—Length: Approximately 3.0 cm. Width: Approximately 1.7 cm. Texture of inner surface: Glabrous. Texture of outer surface: Moderately pubescent. Color of inner surface: NN155A with splotches of 71A. Color of outer surface: 71A to 71B with NN155D at base.

*Calyx*.—Shape: Cupped. Length: Approximately 1.0 cm. Diameter: Approximately 8.0 mm.

*Sepals*.—Quantity per flower: 5. Apex: Acute. Base: Truncate. Length: Approximately 1.0 cm. Width: Approximately 5.0 mm. Texture of inner surface:

Glabrous. Texture of outer surface: Moderately glandular pubescent. Gland color: Colorless, transparent, hairs 71A. Color of inner surface: 138A. Color of outer surface: 138B, appears to have a reddish overlay due to pubescence color.

*Pedicel*.—Strength: Strong, flexible. Aspect: At an acute angle. Length: Approximately 1.0 cm. Diameter: Approximately 1.0 mm. Texture: Densely glandular pubescent. Gland color: Colorless, transparent, hairs 71A. Color: 145A, appears to have a reddish overlay due to pubescence color.

*Reproductive organs*.—Androecium: Stamen quantity: 5 per flower, one lacking an anther, connate by filaments. Stamen length: Approximately 2.4 cm. Filament length: Approximately 2.3 cm. Filament length of fixed portion: Approximately 6.0 mm. Filament color: NN155B. Anther shape: Horseshoe-like. Anther length: Approximately 3.0 mm. Anther color: 79B. Pollen amount: Abundant. Pollen color: NN155D. Gynoecium: Pistil quantity: 1 per flower. Pistil length: Approximately 2.5 cm. Stigma shape: Conical. Stigma length: Less than 1.0 mm. Stigma color: NN155D. Style length: Approximately 2.0 cm. Style color: NN155D with an overlay of 71A that fades away toward stigma. Ovary length: Approximately 5.0 mm. Ovary color: N144C.

Seed and fruit production: Neither seed nor fruit production has been observed.

Disease and pest resistance: Resistance to pathogens and pests common to *Penstemon* has not been observed.

What is claimed is:

1. A new and distinct cultivar of *Penstemon* plant named 'Florpenmag', substantially as herein illustrated and described.

* * * * *